United States Patent [19]

Kato

[11] Patent Number: 4,628,049
[45] Date of Patent: Dec. 9, 1986

[54] FUNGICIDAL COMPOSITION COMPRISING A SYNERGISTIC MIXTURE OF A CYCLOIMIDE FUNGICIDE AND TOLCLOFOS-METHYL

[75] Inventor: Toshiro Kato, Takarazuka, Japan

[73] Assignee: Sumitomo Chemical Company, Limited, Osaka, Japan

[21] Appl. No.: 601,684

[22] Filed: Apr. 18, 1984

[30] Foreign Application Priority Data

May 13, 1983 [JP] Japan .................................. 58-84457

[51] Int. Cl.[4] ...................... A01N 43/38; A01N 57/10
[52] U.S. Cl. .................................... 514/147; 514/421
[58] Field of Search ................ 424/225, 274; 514/147, 514/421

[56] References Cited

U.S. PATENT DOCUMENTS 4,009,278  2/1977  Fujinami et al. ...................... 424/46
4,039,635  8/1977  Kato et al. ........................... 424/225

OTHER PUBLICATIONS

The Pesticide Manual, 6th Edition, (1979), pp. 108, 182, 307, 437, 544.

*Primary Examiner*—Allen J. Robinson
*Attorney, Agent, or Firm*—Stevens, Davis, Miller & Mosher

[57] ABSTRACT

A fungicidal composition containing as an active ingredient a mixture of a cyclic imide fungicide and a fungicide selected from O,O-dimethyl O-(2,6-dichloro-4-methylphenyl) phosphorothioate, 2,6-dichloro-4-nitroaniline and 1,4-dichloro-2,5-dimethoxybenzene in the ratio of 1:0.1 to 1:10 by weight in a total amount of 1 to 90% by weight, and an inert carrier or diluent.

3 Claims, No Drawings

FUNGICIDAL COMPOSITION COMPRISING A SYNERGISTIC MIXTURE OF A CYCLOIMIDE FUNGICIDE AND TOLCLOFOS-METHYL

The present invention relates to an agricultural and horticultural fungicidal composition containing as an active ingredient a cyclic imide fungicide and a fungicide selected from 0,0-dimethyl 0-(2,6-dichloro-4-methylphenyl)phosphorothioate (hereinafter referred to as tolclofos-methyl), 2,6-dichloro-4-nitroaniline (hereinafter referred to as DCNA) and 1,4-dichloro-2,5-dimethoxybenzene (hereinafter referred to as chloroneb) and an inert carrier or diluent.

Cyclic imide fungicides, for example N-(3,5-dichlorophenyl)-1,2-dimethylcyclopropane-1,2-dicarboximide (hereinafter referred to as procymidone), 3-(3,5-dichlorophenyl)-N-isopropyl-2,4-dioxoimidazolidine-1-carboxamide (hereinafter referred to as iprodione), 3-(3,5-dichlorophenyl)-5-methyl-5-vinyloxazolidine-2,4-dione (hereinafter referred to as vinclozolin), 3-(3,5-dichlorophenyl)-5-methyl-5-ethoxycarbonyloxazolidine-2,4-dione (hereinafter referred to as chlozolinate), 3-(3,5-dichlorophenyl)-5-methyl-5-methoxymethyloxazolidine-2,4-dione (hereinafter referred to as myclozolin), etc., have excellent effect in controlling the diseases of crops, particularly gray mold (*Botrytis cinerea*) of tomato, cucumber, eggplant, pimento, strawberry, etc. cultivated in plastic greenhouses and gray mold (*Botrytis cinerea*) of grape, and they are widely used as agricultural and horticultural fungicides. In recent years, however, with these cyclic imide fungicides, the phenomenon of a reduction in controlling effect has come also to be noticed like many other fungicides because of the generation of fungicide-tolerant pathogens due to repeated use. Many trials to overcome this phenomenon such as alternate application of different kinds of fungicides, improvement in the effect by addition of auxiliaries, application of mixed agents, development of new formulation, etc. are being made, but either of them does not yet always come to obtain a sufficient controlling effect (Y. Nagai and T. Takeuchi: Noyaku Kenkyu, Vol. 28, No. 2, 21-27, 1981).

In view of the present situation like this, the present inventors extensively studied to find fungicides from which a sufficient controlling effect can be expected even in fields wherein fungicide-tolerant pathogens are being generated. As a result, it was found that the present composition containing the cyclic imide fungicide and tolclofos-methyl, DCNA or chloroneb as an active ingredient can display a sufficient controlling effect on many plant diseases other than gray mold, and particularly that said composition can be a useful fungicide even in fields wherein, because of vigorous generation of fungicide-tolerant pathogens, a sufficient controlling effect cannot be expected from the conventional fungicides.

The present composition containing as an active ingredient a mixture of tolclofos-methyl, DCNA or chloroneb with the cyclic imide fungicide in a rate of 0.1 to 10 parts by weight, preferably 0.2 to 5 parts by weight of the former based on 1 part by weight of the latter, have also a controlling effect on various plant diseases other than gray mold (*Botrytis cinerea*) of tomato, cucumber, eggplant, pimento, lettuce, red pepper, melon, strawberry, orange, grape, rose, cyclamen, etc., for example helminthosporium leaf spot of rice (*Cochliobolus miyabeanus*), sheath blight of rice (*Rhizoctonia solani*), snow blight of wheat and barley (*Typhula* sp.), blossom blight of apple (*Sclerotinia mali*), brown rot of peach (*Sclerotinia cinerea*), southern blight of tomato, eggplant, water melon, konnyaku, chrysanthemum, etc. (*Corticium rolfsii*), damping-off of cucumber, sugar beet, tomato, etc. (*Rhizoctonia solani*), sclerotinia rot of cucumber, kidney bean, Adzuki bean, etc. (*Sclerotinia sclerotiorum*), black scurf of potato (*Rhizoctonia solani*), root rot of sugar beet (*Rhizoctonia solani*) and the like. The present composition, therefore, can widely be used as a fungicide for paddy field, plowland, orchard, tea garden, pasture, turf and the like.

When the present composition is used as an agricultural and horticultural fungicide, it is formulated into any composition form such as emulsifiable concentrates, wettable powders, suspension formulations, granules, dusts, etc. by mixing with an inert carrier or diluent such as a solid or liquid carrier, a surface active agent and other auxiliaries for formulation.

The content of an active ingredient, contained in the present composition is 1 to 90% by weight, preferably 2 to 80% by weight.

The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, acetonitrile, water and the like.

The surface active agent used for emulsification, dispersion, wetting, etc. includes for example anionic surface active agents such as salts of alkyl-sulfate, alkyl-(aryl)sulfonates, dialkyl sulfosuccinates, salts of polyoxyethylene alkylaryl ether phosphoric acid ester, naphthalenesulfonic acid/formalin condensation products, etc., and nonionic ones such as polyoxyethylene alkyl ether, polyoxyethylene polyoxypropylene block copolymers, sorbitan fatty acid esters, polyoxyethylene sorbitan fatty acid esters, etc. The auxiliaries for formulation include for example lignosulfonates, alginates, polyvinyl alcohol, gum arabic, CMC (carboxymethyl cellulose), PAP (isopropyl acid phosphate) and the like.

Practical embodiments of the present composition are illustratively shown in the following examples wherein parts are by weight.

FORMULATION EXAMPLE 1

40 Parts of tolclofos-methyl, 20 parts of procymidone, 3 parts of calcium lignosulfonate, 2 parts of sodium lauryl sulfate and 35 parts of synthetic hydrated silicon dioxide are thoroughly pulverized and mixed together to obtain a wettable powder.

FORMULATION EXAMPLE 2

30 Parts of chloroneb, 30 parts of iprodione, 3 parts of calcium lignosulfonate, 2 parts of sodium lauryl sulfate and 35 parts of synthetic hydrated silicon dioxide are thoroughly pulverized and mixed together to obtain a wettable powder.

FORMULATION EXAMPLE 3

20 Parts of DCNA, 40 parts of vinclozolin, 3 parts of calcium lignosulfonate, 2 parts of sodium lauryl sulfate and 35 parts of synthetic hydrated silicon dioxide are thoroughly pulverized and mixed together to obtain a wettable powder.

FORMULATION EXAMPLE 4

50 Parts of tolclofos-methyl, 25 parts of chlozolinate, 3 parts of calcium lignosulfonate, 2 parts of sodium lauryl sulfate and 20 parts of synthetic hydrated silicon dioxide are thoroughly pulverized and mixed together to obtain a wettable powder.

FORMULATION EXAMPLE 5

1.5 Parts of chloroneb, 0.5 part of vinclozolin, 1 part of synthetic hydrated silicon dioxide, 2 parts of calcium lignosulfonate, 30 parts of bentonite and 65 parts of kaolin clay are thoroughly pulverized and mixed together, well kneaded with water, granulated and then dried to obtain a granule.

FORMULATION EXAMPLE 6

10 Parts of tolclofos-methyl, 15 parts of procymidone, 3 parts of polyoxyethylene sorbitan monooleate, 3 parts of CMC and 69 parts of water are mixed and wet-pulverized until the particle size is reduced to not more than 5 microns to obtain a suspension formulation.

FORMULATION EXAMPLE 7

One part of DCNA, 1 part of procymidone, 88 parts of kaolin clay and 10 parts of talc are thoroughly pulverized and mixed together to obtain a dust.

Present compositions, either as such or as aqueous dilute liquors, are used in foliar treatment or soil treatment, or they are scattered on soil surface as dust or granule and mixed with the soil. Also, an increase in the fungicidal activity can be expected by using them in mixtures with other agricultural and horticultural fungicides. Further, these formulations may also be used in mixtures with insecticides, acaricides, nematocides, herbicides, plant growth regulating agents, fertilizers, soil improvers and the like.

When the present composition is used as an agricultural and horticultural fungicide, the dosage rate of the active ingredient is generally 1 to 50 g per are, preferably 3 to 30 g per are. When the emulsifiable concentrate, wettable powder, suspension formulation or the like is used as aqueous dilute liquors, its application concentration is generally 0.01 to 1.0%, preferably 0.03 to 0.3%, and the granule, dust or the like is used as such without dilution.

The controlling effect on plant diseases of the present composition will be illustrated with reference to the following test examples. Hereupon, the controlling effect of the chemicals is expressed by "control of disease" obtained as follows: The condition of disease of test plant on examination, that is, the degree of spread of the infected area of leaf is observed with the naked eye and graded into five steps, 0, 0.5, 1, 2 and 4, according to the degree of spread; and disease severity and then control of disease are calculated according to the following equations, respectively.

0: No infected area is noticed on the leaf surface.
0.5: Infected area is noticed in less than 5% of the leaf surface area.
1: Infected area is noticed in less than 20% of the leaf surface area.
2: Infected area is noticed in less than 50% of the leaf surface area.
4: Infected area is noticed in not less than 50% of the leaf surface area.

$$\text{Disease severity (\%)} = \frac{\Sigma\left\{\left(\text{disease index}\right) \times \left(\text{number of leaves}\right)\right\}}{\left(\text{number of examined leaves}\right) \times 4} \times 100$$

$$\text{Control of disease (\%)} = 100 - \frac{\left(\text{disease severity in treated plot}\right)}{\left(\text{disease severity in untreated plot}\right)} \times 100$$

TEST EXAMPLE 1

Controlling test on gray mold of cucumber (*Botrytis cinerea*) (preventive effect)

Sandy loam was filled in a plastic pot, and cucumber (var.: Sagamihanjiro) was sowed and cultivated in a greenhouse for 10 days to obtain cucumber seedlings in the cotyledonous stage. The test chemicals in the form of wettable powder were each diluted with water to a prescribed concentration and foliar-sprayed onto the seedlings so that the spray liquor was thoroughly attached to the leaf surface. After spraying, the seedlings were inoculated by putting the disc-inoculum containing *Botrytis cinerea* tolerant to the cyclic imide fungicides. After inoculation, the seedlings were kept at 20° C. for 3 days under a highly humid condition, and the controlling effect was examined. The result is shown in Table 1.

TABLE 1

| Test chemicals | | Concentration of active ingredient (ppm) | Control of disease (%) |
|---|---|---|---|
| Tolclofos-methyl | | 4000 | 0 |
| | | 1000 | 0 |
| | | 250 | 0 |
| DCNA | | 1000 | 34 |
| | | 250 | 23 |
| Chloroneb | | 1000 | 0 |
| | | 250 | 0 |
| Procymidone | | 1000 | 53 |
| | | 250 | 12 |
| Iprodione | | 1000 | 63 |
| | | 250 | 19 |
| Vinclozolin | | 1000 | 59 |
| | | 250 | 25 |
| Chlozolinate | | 1000 | 56 |
| | | 250 | 17 |
| Present composition | Tolclofos-methyl + procymidone | 1000 + 1000 | 96 |
| | | 1000 + 250 | 92 |
| | | 250 + 1000 | 92 |
| | | 250 + 250 | 86 |
| | DCNA + procymidone | 1000 + 1000 | 99 |
| | | 1000 + 250 | 94 |
| | | 250 + 1000 | 95 |
| | | 250 + 250 | 90 |
| | Tolclofos-methyl + iprodione | 1000 + 1000 | 94 |
| | | 1000 + 250 | 90 |
| | Chloroneb + iprodione | 1000 + 1000 | 94 |
| | | 1000 + 250 | 81 |
| | Tolclofos-methyl + vinclozolin | 1000 + 1000 | 96 |
| | | 1000 + 250 | 90 |
| | DCNA + vinclozolin | 1000 + 1000 | 97 |
| | | 1000 + 250 | 94 |
| | Tolclofos-methyl + chlozolinate | 1000 + 1000 | 92 |
| | | 1000 + 250 | 90 |
| | DCNA + chlozolinate | 1000 + 1000 | 99 |
| | | 1000 + 250 | 95 |

TEST EXAMPLE 2

Controlling test on gray mold of tomato (*Botrytis cinerea*) (preventive effect)

Sandy loam was filled in a plastic pot, and tomato (var.: Fukuju No. 2) was sowed and cultivated in a greenhouse for 50 days to obtain tomato seedlings in the 6-leaf stage. The test chemicals in the form of wettable powder were each diluted with water to a prescribed concentration and foliar-sprayed onto the seedlings so that the spray liquor was thoroughly attached to the leaf surface. After spraying, the seedlings were inoculated by putting the disc-inoculum containing *Botrytis cinerea* tolerant to the cyclic imide fungicides. After inoculation, the seedlings were kept at 20° C. for 4 days under a highly humid condition, and the controlling effect was examined. The result is shown in Table 2.

TABLE 2

| Test chemicals | Concentration of active ingredient (ppm) | Control of disease (%) |
| --- | --- | --- |
| Tolclofos-methyl | 4000 | 0 |
|  | 1000 | 0 |
| DCNA | 1000 | 27 |
| Chloroneb | 1000 | 0 |
| Procymidone | 1000 | 48 |
|  | 250 | 10 |
| Iprodione | 1000 | 53 |
|  | 250 | 12 |
| Vinclozolin | 1000 | 53 |
|  | 250 | 19 |
| Chlozolinate | 1000 | 56 |

TABLE 2-continued

| Test chemicals | | Concentration of active ingredient (ppm) | Control of disease (%) |
| --- | --- | --- | --- |
| | | 250 | 12 |
| Present composition | Tolclofos-methyl + procymidone | 1000 + 1000 | 98 |
| | | 1000 + 250 | 96 |
| | Chloroneb + procymidone | 1000 + 1000 | 94 |
| | | 1000 + 250 | 81 |
| | Tolclofos-methyl + iprodione | 1000 + 1000 | 94 |
| | | 1000 + 250 | 94 |
| | DCNA + iprodione | 1000 + 1000 | 97 |
| | | 1000 + 250 | 94 |
| | Tolclofos-methyl + vinclozolin | 1000 + 1000 | 96 |
| | | 1000 + 250 | 94 |
| | Chloroneb + vinclozolin | 1000 + 1000 | 90 |
| | | 1000 + 250 | 83 |
| | Tolclofos-methyl + chlozolinate | 1000 + 1000 | 98 |
| | | 1000 + 250 | 96 |
| | Chloroneb + chlozolinate | 1000 + 1000 | 92 |
| | | 1000 + 250 | 81 |

What is claimed is:

1. A fungicidal composition containing as an active ingredient, 1 to 90% by weight of a mixture of 1 part of N-(3,5-dichlorophenyl)-1,2-dimethylcyclopropane-1,2-dicarboximide and 0.2 to 1.5 parts by weight of 0,0-dimethyl 0-(2,6-dichloro-4-methylphenyl)phosphorothioate, and an inert carrier.

2. The fungicidal composition according to claim 1, wherein the composition contains 2 to 80% by weight of said mixture of N-(3,5-dichlorophenyl)-1,2-dimethylcyclopropane-1,2-dicarboximide and 0,0-dimethyl 0-(2,6-dichloro-4-methylphenyl)phosphorothioate.

3. A method for controlling a plant pathogenic fungus which comprises applying to said fungus a fungicidally effective amount of a fungicidal composition according to claim 1 or 2.

* * * * *